United States Patent [19]

Martin

[11] Patent Number: 4,525,256
[45] Date of Patent: Jun. 25, 1985

[54] PHOTOPOLYMERIZABLE COMPOSITION INCLUDING CATALYST COMPRISING DIKETONE PLUS 4-(N,N-DIMETHYLAMINO)BENZOIC ACID OR ESTER THEREOF

[75] Inventor: Brian Martin, Princeton Junction, N.J.

[73] Assignee: Johnson & Johnson Dental Products Company, East Windsor, N.J.

[21] Appl. No.: 510,134

[22] Filed: Jul. 1, 1983

[51] Int. Cl.$^3$ ............................. C08F 2/48; C08F 2/50
[52] U.S. Cl. .......................... 204/159.18; 204/159.23; 204/159.24; 430/919; 502/172; 502/522
[58] Field of Search ...................... 204/159.18, 159.23, 204/159.24; 502/200, 510, 509, 522, 167, 172

[56] References Cited

U.S. PATENT DOCUMENTS 4,071,424  1/1978  Dart et al. ...................... 204/159.18
4,189,365  2/1980  Schmitt et al. .................. 204/159.23

FOREIGN PATENT DOCUMENTS 0047097  3/1982  European Pat. Off. .

OTHER PUBLICATIONS

Brauer et al., Polymer Preprints, vol. 19, No. 2, Sep. 1978, pp. 585–590.
Brauer et al., Polymer Reprints, vol. 14, No. 21, Sep. 1978, pp. 585–590.
"Quantacure Photoinitiators", Ward Blenkinsop & Co. Ltd., London, England.

Primary Examiner—Allan M. Lieberman
Attorney, Agent, or Firm—Charles J. Metz

[57] ABSTRACT

There is described a photopolymerizable composition which contains at least one olefinically unsaturated compound and a photosensitive catalyst containing a diketone plus 4-(N,N-dimethylamino)benzoic acid or lower alkyl ester thereof.

10 Claims, No Drawings

PHOTOPOLYMERIZABLE COMPOSITION INCLUDING CATALYST COMPRISING DIKETONE PLUS 4-(N,N-DIMETHYLAMINO)BENZOIC ACID OR ESTER THEREOF

The invention relates to a photopolymerizable composition which contains at least one olefinically unsaturated compound and a photosensitive catalyst containing a diketone plus 4-(N,N-dimethylamino)benzoic acid or lower alkyl ester thereof.

BACKGROUND OF THE INVENTION

The use of photopolymerizable compositions for end use applications such as dental composites is of commercial interest because such compositions can be marketed as one-package systems and therefore do not need to be mixed at the point of use such as is the case with the usual peroxide curable composition which must be mixed with an activator just before use.

This invention is directed to the provision of a photopolymerizable composition containing a catalyst system that is highly effective when employed in conjunction with visible light, and which exhibits rapid cure rate and excellent properties after cure.

SUMMARY OF THE INVENTION

The invention provides a photopolymerizable composition comprising at least one olefinically unsaturated compound and a photosensitive catalyst comprising:

(a) at least one vicinal diketone, preferably selected from the group consisting of camphoroquinone, benzil, and biacetyl; and (b) 4-(N,N-dimethylamino)benzoic acid or lower alkyl ester thereof.

THE PRIOR ART

The manufacturer of the ethyl and the n-butyl esters of 4-(N,N-dimethylamino)benzoic acid recommends their use with certain monoketone compounds as photoactivators for ultraviolet light-curable resin formulations.

Brauer et al., in Polymer Preprints, Vol. 19, No. 2, September 1978, pages 585–590, disclose the evaluation of 4-(N,N-dimethylamino)benzoic acid as an amine accelerator for peroxide cured dental composites.

Dart et al., in U.S. Pat. No. 4,071,424, describes photosensitive catalysts comprising diketone compounds plus tertiary amines. Preferably, the Dart et al. tertiary amines are free of aromatic groups attached directly to the amino nitrogen (e.g., see Col. 5, lines 29–35 of the Dart et al. patent).

Photopolymerizable compositions useful as dental restorative compounds are described in a number of patents, for example, in Schmitt et al., U.S. Pat. No. 4,189,365. See also European Patent application No. 0047097, published on Mar. 10, 1982.

DETAILED DESCRIPTION OF THE INVENTION

The photopolymerizable composition of the invention includes at least one olefinically unsaturated compound. Such materials are well known in the art, and need to be illustrated only by a few examples. When the composition of the invention is designed for use in a dental restorative material, it is preferred that the olefinically unsaturated compound by an acrylic or methacrylic ester, and particularly, a compound having two or more acrylic or methacrylic ester groups because the polyfunctional acrylic esters exhibit less shrinkage upon polymerization than do the monofunctional acrylic esters, and also provide cross-linking. Specific types of acrylic esters that are useful include alkane diol acrylates or methacrylates such as the $C_4$–$C_{12}$ alkane diol acrylates or methacrylates, e.g., 1,10-decamethylene diol dimethacrylate and 1,6-hexamethylene diol dimethacrylate; the polyalkylene glycol acrylates or methacrylates, such as triethylene glycol dimethacrylate and tetraethylene glycol dimethacrylate; bisphenol-A acrylate or methacrylate esters; alkoxylated bisphenol-A acrylate or methacrylate, e.g., ethoxylated bisphenol-A dimethacrylate; bisphenol-A diglycidyl dimethacrylate ("bis-GMA"); and the like. Other multifunctional acrylic or methacrylic esters that can be used include methacrylate-terminated polyurethanes, trimethylolpropane trimethacrylate or triacrylate, and the like.

The catalyst composition employed in the invention includes at least one vicinal diketone compound, preferably selected from the group consisting of camphoroquinone, benzil and biacetyl. Combined with this diketone compound is 4-(N,N-dimethylamino)benzoic acid or a lower alkyl (e.g., $C_1$–$C_4$ alkyl) ester thereof. The ethyl ester is preferred. The catalysts are employed in catalytically effective amounts, such as from about 0.1 to about 5 weight percent (based on weight of olefinically unsaturated compound) of the diketone compound, plus from about 0.1 to about 5 weight percent (again, based on the weight of the olefinically unsaturated compound) of the 4-(N,N-dimethylamino)benzoic acid or ester thereof.

The composition of the invention can contain fillers such as silica, powdered glass, powdered quartz, or the like, which are conventional in the art.

The catalyst system is activated by exposure to light of a wave length of from about 250 nm to about 700 nm. Preferably, the wave length is in the visible light region (about 380 nm to 550 nm). The visible light sources ordinarily used for visible light-cured dental composites can be used with this catalyst system. The examples below illustrate one such light sources and the conditions under which they are used.

The following examples illustrate the practice of the invention:

EXAMPLE 1 AND CONTROL 1

The cure rates and degrees of cure (as evidenced by hardness) of photopolymerizable resin systems containing either ethyl 4-(N,N-dimethylamino)benzoate ("EDMAB") or N,N-dimethylaniline ("DMA"—disclosed as a photoactivator by Dart et al. in U.S. Pat. No. 4,071,424), were compared. The resin formulation used was the following:

TABLE I

| Component | Parts by Weight |
| --- | --- |
| Ethoxylated bisphenol-A dimethacrylate ("EBAD") | 24 |
| Silane-treated Quartz filler[1] | 66.2 |
| Silane-treated Colloidal silica[2] | 9.8 |
| Diketone Photoinitiator[3] | 0.069 |

TABLE I-continued

| Component | Parts by Weight |
|---|---|
| Amine Photoactivator | Varied |

[1]Quartz powder, average diameter 13 microns, treated with 3 weight percent A-174 silane (gamma-methacryloxypropyltrimethoxysilane - Union Carbide Corporation).
[2]"AEROSIL" R972 (Degussa Corporation), a silane-coated silica.
[3]A 70:30 (wt/wt) mixture of camphoroquinone:benzil.

The resin formulations were placed in a brass mold to form a 3-millimeter thick layer. They were activated by a 20-second exposure to a commercial visible light source ("Prisma-Lite", L. D. Caulk Company) designed for dental applications. The actual light source was a quartz projector lamp whose spectral output starts at 400 nm and continues through the visible part of the spectrum. Peak output is at 480 nm. The light is delivered through a fiber optic rod. The end of the fiber optic rod was held about 1 mm away from the surface of the composite mixture.

The cured samples were aged for 1 hour in 37° C. water, after which the hardness of the underside of each sample was measured (Rockwell T-15 scale). The time to peak exotherm, as measured by a differential scanning calorimeter ("DSC"), was determined. The results are set forth in Table II:

TABLE II

| SAMPLE | Amine; Parts by Weight[4] | Cure Time, Seconds | Hardness, Rockwell T-15 |
|---|---|---|---|
| Example 1 | EDMAB; 0.6 | — | 63 |
|  | EDMAB; 1.2 | 29.4 | 61 |
| Control 1 | DMA; 0.5 | 27.6 | 47.5 |
|  | DMA; 1.2 | 35.4 | — |
|  | DMA; 3.0 | 52.8 | 45.2 |

[4]Expressed as percent of total monomer.

As these data indicate, EDMAB yields a harder cured composite than DMA, presumably because of a more efficient and complete polymerization.

EXAMPLE 2 AND CONTROLS 2-4

It has been observed that photopolymerizable resin systems have a tendency to gradually lose their activity during storage. The compositions of this invention seem to be less prone to this problem, as is evidenced by accelerated aging tests. The resin formulation described above as Example 1, a similar formulation in which N,N-dimethylaminoethyl methacrylate ("DMAEM") was used as the amine photoactivator, and two commercial photopolymerizable dental composite formulations were evaluated for cure times and hardness (as described in Example 1), both as freshly prepared (or purchased), and after the uncured formulations had undergone accelerated aging by being stored at 80° C. for 1, 2, 3, and 4 weeks. The results are set forth below in Table III:

TABLE III

Effect of Accelerated Aging of Formulation on Cure time and Composite Hardness

| Sample | Initial Properties | | 1 Week | 2 Weeks | | 3 Weeks | 4 Weeks |
|---|---|---|---|---|---|---|---|
|  | Cure Time | Hardness | Cure Time | Cure Time | Hardness | Cure Time | Hardness |
| Example 2 | | | | | | | |
| 0.4% EDMAB | 17 | 62 | 18 | 18 | 64 | 19 | 59 |
| 0.6% EDMAB | 17 | 63 | 17 | 19 | 63 | 19 | 59 |
| 0.8% EDMAB | 16 | 62 | 17 | 20 | 66 | 19 | 61 |
| 1.0% EDMAB | 17 | 63 | 17 | 18 | — | 19 | 62 |
| 1.2% EDMAB | 17 | 61 | 16 | 17 | 66 | 18 | 63 |
| Controls 2-4 | | | | | | | |
| 2.5% DMAEM[5] | 22 | 59 | 27 | 29 | 54 | 27 | 55 |
| Commercial Resin A | 30 | 62 | 33 | 27 | 60 | 30 | 57 |
| Commercial Resin B | 25 | 62 | 26 | 25 | 63 | 25 | 56 |

[5]This formulation contained 0.6 part by weight of a 50:50 mixture of camphoroquinone:benzil.

EXAMPLE 3 AND CONTROLS 5 AND 6

1. Monomer Mix Formulation

Three monomer systems differing in the photoinitiator type and contents were prepared by the following procedure:

50 grams of EBAD were added to a 100 ml beaker fitted with a magnetic stirring bar and the resin was heated to 40°-45° C. to lower the viscosity and enhance the dissolution of the photoinitiators. Weighed amounts (see Table IV) of the various initiators were added directly to the monomer and stirring continued in the dark until the solids had dissolved (~20 min). After dissolution was complete the mix was placed in a vacuum oven and degassed by evacuation. When the samples ceased to bubble, they were assumed to be clear of air and were packaged in brown glass bottles.

TABLE IV

| Sample | Monomer | Photoinitiators | Conc. (g/g × 100) |
|---|---|---|---|
| Control 5 | EBAD | Camphoroquinone | 0.25 |
|  |  | DMAEM | 2.50 |
| Control 6 | EBAD | Camphoroquinone | 0.30 |
|  |  | Benzil | 0.30 |
|  |  | DMAEM | 2.40 |
| Example 3 | EBAD | Camphoroquinone | 0.28 |
|  |  | Benzil | 0.12 |
|  |  | EDMAB | 1.20 |

2. Set Time, Degree of Conversion

Cure time and heat of polymerization were determined using a DuPont model 910 DSC (differential scanning calorimeter) linked to a DuPont 990 temperature controller/chart recorder. Photoactivated monomer was poured into a 1.5×6 mm aluminum sample pan and placed on the sample thermocouple, with an empty pan serving as a reference mass. Sample and reference were heated to 37° C. ($T_c$ or temperature of cure) and held isothermally in the dark until the scan baseline had equilibrated. The top of the DSC sample chamber was fitted with a transparent cover of 1 mm thick borosilicate glass, allowing light to enter but preventing excessive sample chamber heat loss and air circulation. The sample was illuminated for 45 seconds with a PRIMSMA ® (L. D. Caulk) light positioned 8 mm above the pan and 2 mm above the window. Cure exotherms were recorded as a plot of calories over time. Set time was measured as the distance in centimeters from the start of illumination to exotherm peak multiplied by the timebase setting in min/cm.

Cure enthalpy ($\Delta H_t$) was determined by calculating the integrated area of the exotherm divided by the sample mass, and multiplied by specific machine constants. After initial light cure, the sample was held at 37° C. for 30 minutes and then cooled to approximately 30° C. where it was held for 5 minutes. The sample was then heated at a program rate of 10° C./minutes until a second exotherm was recorded. The enthalpy of this residual curing was determined ($\Delta H_{resid.}$) and added to the initial cure exotherm to give the heat of reaction ($\Delta H_{rxn}$) for the resin system at a 45 seconds light exposure. Degree of conversion ($\alpha$) was calculated as:

$$\alpha 45 \text{ sec.} = \frac{\Delta H_t}{\Delta H_{rxn}} \times 100$$

where $\alpha$ represents the amount of reaction a particular resin system would undergo at some cure temperature (Tc) when exposed to illumination of known duration. In all cases the experimental variables were kept constant, (i.e. $T_c$, length of illumination, aging time) and only the resins themselves varied in formulation. Three repeats were made for each resin system and the averages and standard deviations calculated. Values for set time, $\Delta H_t$, $\Delta H_{resid}$, and $\alpha$ are listed in Table V.

TABLE V

RESULTS OF DSC ANALYSIS

| Sample | Time to Peak, seconds | Cure Enthalpy $\Delta H_t$ (cal./g) | Residual Cure $\Delta H_{resid.}$ (cal./g) | Degree Conversion $\frac{\Delta H_t}{\Delta H_{rxn}} \times 100$ |
|---|---|---|---|---|
| Control 5 | 12.9 s.d. = 0.5 | 57.9 s.d. = 0.6 | 8.70 s.d. = 0.7 | 86.9 s.d. = 0.8 |
| Control 6 | 6.6 s.d. = 0.5 | 58.5 s.d. = 0.6 | 7.46 s.d. = 0.5 | 88.7 s.d. = 0.5 |
| Example 3 | 7.7 s.d. = 0.5 | 54.15 s.d. = 0.6 | 6.06 s.d. = 0.5 | 90.0 s.d. = 0.5 |

(s.d represents standard deviation)

These results indicate a slightly, but significantly, higher degree of cure for the photoinitiators used in Example 3 than for the photoinitiators used in Controls 5 and 6.

3. Stress/Strain Testing, Hardness

Flexural modulus and strength were determined for the three resin systems filled with 67.5% <5 micron quartz treated with 3.0% A-174 silane. The composites were prepared as follows: to 10.0 grams of resin was added 21.0 grams of filler with constant stirring. As soon as all the filler was incorporated, the pastes were degassed in a vacuum oven until all bubbling ceased. They were then removed and mixed thoroughly to disperse the filler and produce a smooth paste (5.0 minutes). After mixing, they were returned to the vacuum chamber and degassed a second time until they appeared void-free by microscopic examination. Flexural test bars were made by curing the pastes in Teflon molds between glass slides with exposure to an unshielded FOTOFIL ® light (spectral output from 400 nm through the visible range, with a peak at 600 nm) for 60 seconds on each side. Samples were aged for 24 hours in deionized water at 37° C. and run on an Instron HP-11 stress/strain testing apparatus for flexural strength and modulus. Rockwell Hardness (F scale) was determined for the broken flexural samples, saved as retains for that purpose. Results of Instron and Rockewll testing are listed in Table VI:

TABLE VI

FLEXURAL TESTING DATA

| Material Code | Flexural Strength (MPa) | Flexural Modulus (MPa) | Hardness ($R_f$ scale) |
|---|---|---|---|
| Composite A (Control 5 + 67.5% Quartz) | $\bar{x}$ = 117.0 n = 8 s.d. = 9.5 | $\bar{x}$ = 11036 n = 8 s.d. = 1086 | $\bar{x}$ = 80.9 n = 8 s.d. = 1.67 |
| Composite B (Control 6 + 67.5% Quartz) | $\bar{x}$ = 127.4 n = 8 s.d. = 11.6 | $\bar{x}$ = 10658 n = 8 s.d. = 1116 | $\bar{x}$ = 82.3 n = 8 s.d. = 0.96 |
| Composite C (Example 3 + 67.5% Quartz) | $\bar{x}$ = 153.5 n = 8 s.d. = 5.6 | $\bar{x}$ = 14008 n = 8 s.d. = 870 | $\bar{x}$ = 87.6 n = 8 s.d. = 1.16 |

($\bar{x}$ represents the arithmetic mean of n samples.)

As these data show, the composite which contained the Example 3 photoinitiators had substantially higher flexural strength, flexural modulus, and hardness than the composites which contained the Control 5 and 6 photoinitiators. This demonstrates a significant increase in cure efficiency through the use of the photoinitiators which are the subject of this invention.

What is claimed is:

1. A photopolymerizable composition comprising at least one olefinically unsaturated compound and a catalytically effective amount of a photosensitive system consisting essentially of:
    (a) an effective amount of at least one vicinal diketone compound; and
    (b) an effective amount of 4-(N,N-dimethylamino)-benzoic acid or lower alkyl ester thereof.

2. The photopolymerizable composition of claim 1 comprising a dental restorative composition, wherein the olefinically unsaturated compound comprises a compound containing at least two acrylate or methacrylate groups.

3. The photopolymerizable composition of claim 1 wherein the diketone is camphoroquinone, benzil, biacetyl, or mixture thereof.

4. The photopolymerizable composition of claim 2 wherein the diketone is camphoroquinone, benzil, biacetyl, or mixture thereof.

5. The photopolymerizable composition of claim 1 wherein said component (b) is ethyl 4-(N,N-dimethylamino)benzoate.

6. The photopolymerizable composition of claim 2 wherein said component (b) is ethyl 4-(N,N-dimethylamino)benzoate.

7. The photopolymerizable composition of claim 3 wherein said component (b) is ethyl 4-(N,N-dimethylamino)benzoate.

8. The photopolymerizable composition of claim 4 wherein said component (b) is ethyl 4-(N,N-dimethylamino)benzoate.

9. The photopolymerizable composition of claim 2 wherein the catalyst is a mixture of benzil, camphoroquinone, and ethyl 4-(N,N-dimethylamino)benzoate.

10. The photopolymerizable composition of claim 1 wherein said vicinal diketone compound is employed in an amount within the range of from about 0.1 to about 5 weight percent, based on weight of olefinically unsaturated compound, wherein said 4-(N,N-dimethylamino)benzoic acid or lower alkyl ester thereof is employed in an amount within the range of from about 0.1 to about 5 weight percent, based on weight of olefinically unsaturated compound, and wherein said lower alkyl is $C_1$ to $C_4$ alkyl.

* * * * *

UNITED STATES PATENT AND TRADEMARK OFFICE
CERTIFICATE OF CORRECTION

PATENT NO. : 4,525,256
DATED : June 25, 1985
INVENTOR(S) : Brian Martin

It is certified that error appears in the above-identified patent and that said Letters Patent is hereby corrected as shown below:

Claim 1, Col. 1, line 27, after the word "photosensitive" insert --catalyst--.

Signed and Sealed this

Twenty-second Day of October 1985

[SEAL]

Attest:

DONALD J. QUIGG

Attesting Officer

Commissioner of Patents and
Trademarks—Designate